United States Patent [19]

McPherson et al.

[11] Patent Number: 4,816,442

[45] Date of Patent: Mar. 28, 1989

[54] METHOD OF INHIBITING TUMOR GROWTH SENSITIVE TO CIF-β TREATMENT

[75] Inventors: John M. McPherson, Sunnyvale, Calif.; Danile R. Twardzik, Bainbridge Island; George J. Todaro, Seattle, both of Wash.; Karl A. Piez, Menlo Park, Calif.; Jane E. Ranchalis, Seattle, Wash.

[73] Assignee: Collagen Corporation, Palo Alto, Calif.

[21] Appl. No.: 928,760

[22] Filed: Nov. 7, 1986

[51] Int. Cl.$^4$ .............................................. A61K 37/00
[52] U.S. Cl. .......................................... 514/12; 514/2
[58] Field of Search ...................................... 514/2, 12

[56] References Cited

FOREIGN PATENT DOCUMENTS 0169016 1/1986 European Pat. Off. ................ 514/2

OTHER PUBLICATIONS

E. J. J. van Zoelen et al., *J Biol Chem* (4/86) 261:5003-09.
D. S. Saloman et al., *Cancer Invest* (1/86) 4:43-60.
R. K. Assoian et al., *Cancer Cells* 3 (6/85) 59-64.
H. L. Moses et al., *Cancer Cells* 3 (6/85) 65-71.
R. F. Tucker et al., *Science* (1984) 226:705-07.
R. K. Holley et al., *Cell Biol Int Rep* (1983) 7:525-26 (I), 7:141-47 (II).
A. W. Hamburger et al., *Science* (1977) 197:461-63.

Primary Examiner—Jerome D. Goldberg
Attorney, Agent, or Firm—Ciotti & Murashige, Irell & Manella

[57] ABSTRACT

Polypeptides called cartilage-inducing factors (CIFs) that are found in bone and have heretofore been identified as having in vitro cartilage-inducing activity, TGF-β activity, and anti-inflammatory activity have now been found to possess potent oncostatic activity. The CIFs showed oncostatic activity on human and animal tumors, including carcinomas, adenocarcinomas, lymphomas, and melanomas.

3 Claims, 1 Drawing Sheet

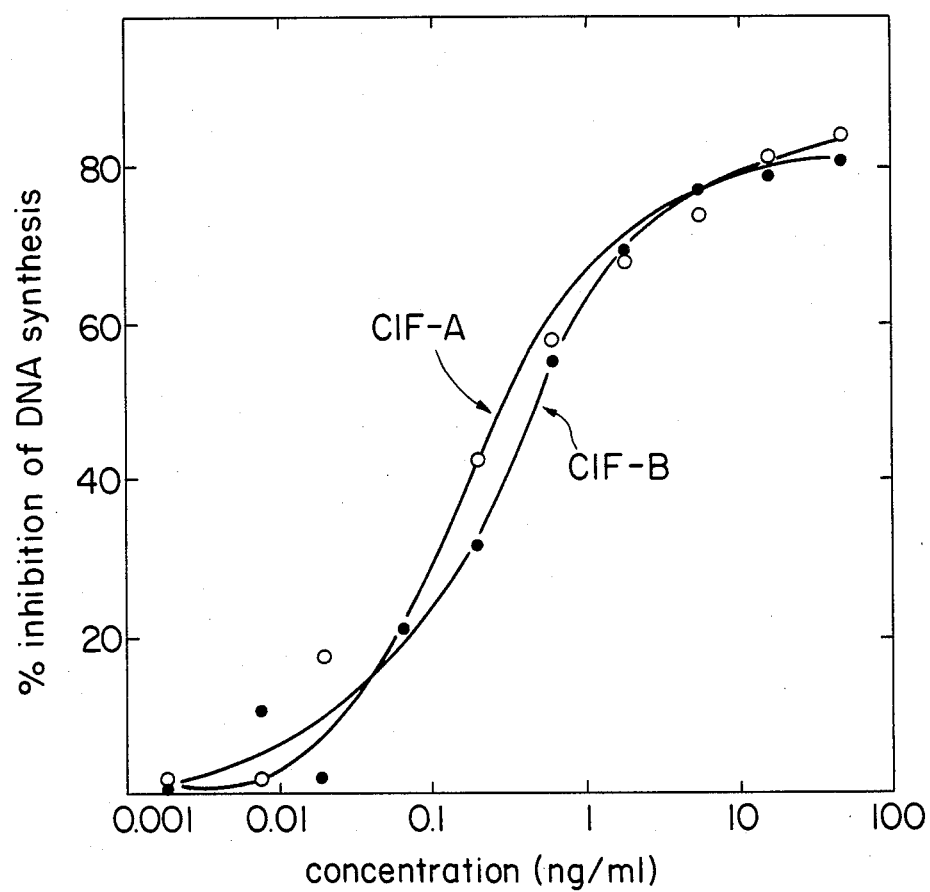

METHOD OF INHIBITING TUMOR GROWTH SENSITIVE TO CIF-β TREATMENT

DESCRIPTION

TECHNICAL FIELD

This invention is in the field of cancer treatment. More particularly it relates to a method of inhibiting tumor growth using polypeptides heretofore referred to as cartilage-inducing factors (CIFs).

BACKGROUND

European patent application No. 85304848.6 (published Jan. 22, 1986 under publication number 0169016) describes two bovine bone-derived CIFs, designated CIF-A and CIF-B. Both have molecular weights of approximately 26,000 daltons by SDS-PAGE analysis and are dimers. They each exhibit in vitro chondrogenic activity by themselves, as measured by cartilage specific proteoglycan (PG) production in an agarose gel culture model using fetal rat mesenchymal cells. Neither, however, is chondrogenically active in vivo by itself. Amino acid sequencing of CIF-A showed that it has a partial (30 amino acids) N-terminal sequence identical to that reported for a human placenta-derived polypeptide called beta-type transforming growth factor (TGF-β). The partial N-terminal sequence of CIF-B is different from that of TGF-β (eleven of the first 30 amino acids at the N-terminus are different). Both CIFs exhibit activity in the TGF-β assay (ability to induce anchorage-independent growth of normal rat kidney cell colonies in soft agar).

Copending U.S. patent application Ser. No. 836,672 filed Mar. 6, 1986 discloses that both CIFs possess anti-inflammatory activity and are inhibitors of mitogen-stimulated T cell proliferation and B cell activation. It also reports that CIF is localized in centers of hematopoiesis and lymphopoiesis and that CIF may, therefore, be useful for treating indications associated with malfunction or dysfunction of hematopoiesis or lymphopoiesis.

TGF-β derived from bovine kidney, human placenta, and human platelets is described in International patent application No. PCT/US83/01460, published Mar. 29, 1984 under no. WO84/01106, EPA No. 84450016.5, published Dec. 19, 1984 under No. 0128849, and U.S. patent applications Ser. Nos. 500,832, 500,833, and 500,927, filed June 3, 1983. These applications present data showing that such TGF-β, when combined with EGF or TGF-αL, promotes cell proliferation in the above mentioned soft agar culture assay and promotes cell proliferation and protein deposition in a rat soft tissue wound healing model.

TGF-β has been shown to be very similar to, if not identical to a polypeptide identified as growth inhibitor (GI) purified from BSC-1 monkey kidney cell-conditioned medium (Tucker, R. F. et al, Science (1984) 226:705). TGF-β and GI have both shown the ability to inhibit growth of a variety of tumor cell lines (Assoian, R. K. et al, Cancer Cells 3/ Growth Factors and Transformation, Cold Spring Harbor Laboratory, June 1985, pages 59-64 and Moses, H. L. et al, Cancer Cells 3/ Growth Factors and Transformation, ibid, pages 65-71).

U.S. patent application Ser. No. 602,520, filed Apr. 20, 1984, describes a group of factors referred to as tumor inhibiting factors (TIFs). These factors were partially isolated from serum-free conditioned media derived from the human tumor cell line A673. The factors are reported to have molecular weights of 28,000 daltons, 10–16,000 daltons and 5–10,000 daltons, to be antagonistic to the activity of TGFs on anchorage independent growth of tumor cells in soft agar, and to inhibit in vitro proliferation of various human and animal tumors.

The present invention is based on the findings that CIF-A and CIF-B possess oncostatic activity.

DISCLOSURE OF THE INVENTION

One aspect of the invention is a method of inhibiting growth of tumor cells in a mammal comprising administering an oncostatically effective amount of CIF or a mixture of CIFs to the mammal.

Another aspect of the invention is a method of inhibiting growth of tumor cells in a mammal comprising administering an oncostatically effective amount of CIF-A to the mammal.

Still another aspect of the invention is a method of inhibiting growth of tumor cells in a mammal comprising administering an oncostatically effective amount of CIF-B to the mammal.

BRIEF DESCRIPTION OF THE DRAWING

FIG. 1 is a graph of the test results of Example 1, infra.

MODES FOR CARRYING OUT THE INVENTION

The purification to homogeneity of CIF-A and CIF-B from demineralized bone and the characterization of the pure polypeptides are described in European patent application Publication No. 0169016 (corresponding to U.S. patent application Ser. No. 767,144 filed Aug. 19, 1985), the disclosure of which is incorporated herein by reference.

CIF-A is apparently a homodimer having a molecular weight of approximately 26,000 daltons as determined by SDS-PAGE. It has the following N-terminal amino acid sequence:

```
1                      5                         10
Ala—Leu—Asp—Thr—Asn—Tyr—Cys—Phe—Ser—Ser—Thr—

15                        20
  —Gln—Lys—Asn—Cys—Cys—Val—Arg—Gln—Leu—Tyr—

25                        30
          —Ile—Asp—Phe—Arg—Lys—Asp—Leu—Gly—Trp.
```

CIF-B is also believed to be a homodimer of approximately 26,000 daltons molecular weight as measured by SDS-PAGE. Its N-terminal amino acid sequence is as follows:

```
1                      5                         10
Ala—Leu—Asp—Ala—Ala—Tyr—Cys—Phe—Arg—Asn—Val—

15                        20
  —Gln—Asp—Asn—(Cys—Cys)—Leu—Arg—Pro—Leu—Tyr—

25                        30
          —Ile—Asp—Phe—Lys—Arg—Asp—Leu—Gly—Trp.
```

Both CIFs are relatively insensitive (in terms of reduction in biological activity) to heat or trypsin treatment, but lose their activity on reduction with agents such as 2-mercaptoethanol or dithiothreitol.

The terms "CIF-A" and "CIF-B" as used herein are intended to include the bovine polypeptides described above, counterpart polypeptides derived from other mammalian species such as humans, pigs, sheep, and horses and synthetic analogs (muteins) of either the bovine or other mammalian polypeptides. The analogs will typically be substantially similar in amino acid sequence (i.e., at least about 90% identity in sequence to the particular native species). These CIFs may be derived from native sources or be prepared by recombinant DNA technology. Recombinant polypeptide may differ from the native polypeptide in manners (e.g., lack of glycosylation) other than in amino acid sequence as is known in the art.

The oncostatic activity of CIFs is, like the other biological activity of CIFs, believed to be nonspecies specific. Thus, CIF of one mammalian species is efficacious when administered to another mammalian species. In order to lessen the likelihood of immunogenicity, however, it is preferred that the polypeptide be of the same species as the subject being treated. While the most common use of CIF-A or CIF-B as an oncostat will be in the treatment of humans suffering from cancer, domestic animals such as cattle, sheep and pigs, and sports or pet animals such as dogs, cats, and horses may be treated for neoplastic conditions.

CIFs may be used as oncostats in treating any type of cellular neoplasm, including, without limitation, carcinomas, myelomas, melanomas, and lymphomas. Particularly preferred targets are breast, lung, colon and ovarian carcinomas. The CIFs may be administered locally or systemically, depending upon the nature and degree of the neoplasm being treated. For local administration an oncostatically effective amount of CIF-A, CIF-B or mixtures thereof formulated with a pharmaceutically acceptable carrier as an injectable for parenteral administration, or as a solid or semi-solid implant which may or may not be of a sustained or controlled release form.

Alternatively the oncostats could be delivered to solid tumors in particular, including inoperable tumors using current catheter technology for localized delivery via the arterial supply to the tumor. In this situation the oncostat could be mixed with a vasoocclusive agent, such as injectable collagen, which would provide a means to reduce perfusion of the tumor and at the same time provide for localized delivery of the oncostatic agent. Clips may also be used to occlude venous drainage, and thus maintain high doses of CIF in the tumor mass.

For systemic administration oncostatically effective amounts of CIF-A, CIF-B or mixtures thereof will be formulated with conventional carriers used for water soluble proteins (e.g., physiological saline, sugar solutions and the like) for injection into circulation. Alternatively, they may be formulated as a sustained release formulation that releases the CIF to circulation over a prolonged time period. Specific targeting of the factor for tumor cells in systemic applications may be accomplished by conjugation of the CIF to an antibody directed against tumor specific cell surface antigen(s). Enhanced tumor cell cytotoxicity may be accomplished by covalently radiolabeling the CIFs with $^{131}I$, a cytotoxic agent. The CIFs are readily iodinated and retain full biological activity. Monoclonal antibody preparations with specificity for particular tumor types, such as breast and ovarian tumors, are well known in the art. Other oncostats or chemotherapeutic drugs may be included in the formulation if desired.

The term "oncostatically effective" is intended to indicate a dose that effects a significant (>50%) inhibition of tumor cell proliferation. In in vitro assays, 50% inhibition is generally observed at CIF concentrations of the order of 0.2 μg/ml and saturation is achieved at 10 μg/ml. Inhibition may be monitored in vivo by monitoring the patient's tumor burden. The amount of CIF which is oncostatically effective in a given treatment will depend upon the patient, the type and degree of cancer being treated and the mode of administration. In general, the amounts administered to adult humans will be in the range of about 0.1 to 1000 μg. When administered locally (e.g., to treat a solid tumor) amounts in the lower portion of this range will normally be used, typically 0.1 to 10 μg. Correspondingly systemic administration will involve the higher segment of the range (0.1–10 μg) due to clearance or other in situ inactivation of the polypeptide.

EXAMPLES

The following examples are intended to further illustrate the oncostatic activity of CIFs. They are not intended to limit the invention in any manner. Abbreviations used in the examples are: Gdn.HCl=guanidine hydrochloride; EDTA=ethylenediamine tetraacetic acid; CM=carboxymethyl; HPLC=high performance liquid chromatography; SDS-PAGE=sodium dodecyl sulfate polyacrylamide gel electrophoresis; DMEM=Dulbecco's modified Eagle's medium; ($^{125}I$)IdUdr=5-[$^{125}I$]iodo-2-deoxyuridine; DNA-deoxyribonucleic acid.

Purification of CIFs

CIF-A and -B were purified from demineralized bone powder as in European patent application No. 85304848.6. Briefly, bovine metatarsal bone was demineralized for 16 hr in 0.5M HCl at 4° C. and peptides solubilized utilizing a 4M Gdn.HCl/1 mM N-ethylmaleimide/10 mM EDTA, pH 6.8 extraction procedure. CIFs were then purified by gel filtration on Sephacryl S-200 columns equilibrated in 4M Gdn.HCl/0.02% sodium azide/10 mM EDTA, pH 6.8 followed by cationic exchange chromatography on CM cellulose using a linear 10–400 mM NaCl gradient in 6M urea/10 mM NaCl/1 mM N-ethylmaleimide/50 mM sodium acetate, pH 4.5. Final purification and resolution of CIF-A from CIF-B was achieved by reversed phase HPLC on $C_{18}$ columns eluted with 0–60% acetonitrile gradient in 0.1% trifluorocetic acid, pH 1.9. Homogeneity was demonstrated by silver stained SDS-PAGE analysis and by amino terminal amino acid sequence analysis.

In Vitro Assay System

Cell lines were cultured on 96-well tissue culture plates at a concentration of $3 \times 10^3$ cells per 50 μl of DMEM containing 10% fetal calf serum. Samples tested were in 0.2M acetic acid and were lyophilized in sterile 12×75 mm tubes for the assay. Samples were resuspended in DMEM with 10% fetal calf serum, the appropriate dilutions made, and were added in 50 μl to the test wells in triplicate 5 hr after plating. After incubation at 37° C. in a humidified 5% $CO_2$-95% air atmosphere for 72 hr ($^{125}I$)IdUdr, a thymidine analogue was added in 10 μl of medium (10 μCi/ml). The cells were incubated an additional 24 hr and at the end of that period were washed 1X with phosphate buffered saline, fixed for 10 min in 200 μl of methanol, and air dried for 15 min. The growth of the cells was measured by the incorporation of ($^{125}$I)IdUdr into the DNA of the cells. The cells were solubilized in 200 μl of 1 M NaOH for 20 min at 60° C. and labelled material collected using the Titertek Supernatant Collection System. Inhibition-stimulation of growth was expressed in the percent decrease or increase of ($^{125}$I)IdUdr incorporation of the treated cells when compared to the incorporation of untreated cells.

Soft Agar Assay

Assays were carried out in DMEM containing 10% fetal calf serum as described by Iwata, K. K., et al, Canc. Res. (1985) 45:2689–2694. A 1 ml base layer of 0.5% agar was poured into 6 well plates. Sterile, lyophilized test samples were resuspended in 750 μl of medium containing cells ($2 \times 10^4$ cells/ml) and 0.3% agar. The mixture was poured onto the base layer and allowed to harden for 15 min at room temperature. Plates were then incubated at 37° C. in a humidified 5% CO$_2$-95% air atmosphere for a period of 1–2 weeks. The wells were scored by counting the number of colonies formed in 8 random lower power fields.

EXAMPLE 1

Pure CIF-A and CIF-B (as determined by SDS-PAGE and amino terminal sequence analysis) were tested at various concentrations on nonconfluent monolayer cultures ($3 \times 10^4$ cells/well) of an established mink epithelial cell line (CCl 64) which had been shown previously to be sensitive to tumor- inhibiting polypeptides. (See U.S. Ser. No. 602,520.) Cultures were pulsed with ($^{125}$I)IdUdr (1 μCi/ml) on day 4 and cultures harvested on day 5 and evaluated as described above (In Vitro Assay System). Identical tests on human platelet-derived TGF-β were carried out for comparison. The results of these tests on CIF-A and CIF-B are shown in FIG. 1. Values for % Inhibition represent the average of triplicate determinations. As shown in FIG. 1, CIF-A and CIF-B elicit identical dose response curves with half maximal inhibition seen at 0.5 ng/ml; saturation (>90% inhibition) is achieved at about 10 ng/ml for both CIF-A and CIF-B. Human platelet-derived TGF-β generated cell dose response curves were similar to both CIFs. In addition, a striking change in cell morphology was observed in CCl 64 monolayer cultures as early as three days post treatment with CIFs. Again, this observed effect was indistinguishable in cultures treated with either CIF-A or CIF-B. In contrast to the untreated controls which exhibit a puffy cuboidal-like morphology, CCl 64 cells treated with 7.8 ng/ml of either CIF-A or CIF-B appear very flattened and display a pheontype very similar to that of normal, flattened lung epithelium.

EXAMPLE 2

Using a concentration of CIF determined from the CCl 64 dose response curve (FIG. 1) that gives a maximal inhibition, a variety of human and nonhuman tumor and "normal" cells were tested for their growth response to CIF-A and CIF-B in the in vitro assay system described above. CIF was added (>10 ng/ml) to plated cells (3000 cells/well) at day 1, pulsed with ($^{125}$I)IdUdr on day four and harvested on day 5. The results of these tests are reported in Table 1 below.

TABLE 1
Effects of CIF-A and CIF-B on the Growth of Different Cell Lines in Culture

| | [$^{125}$I]IdUdr Incorporation | | | |
|---|---|---|---|---|
| | CIF-A | | CIF-B | |
| Cell Line | % inhib | % stim | % inhib | % stim |
| Human tumor | | | | |
| A549 lung carcinoma | 55 | — | 48 | — |
| 2981 lung adeno carcinoma | 52 | — | 46 | — |
| A375 melanoma | 45 | — | 52 | — |
| A431 epidermoid carcinoma | 30 | — | 23 | — |
| MCF-7 | 58 | — | 60 | — |
| A673 rhadomyosarcoma | — | — | — | — |
| Normal | | | | |
| (WI 38) human lung fibroblasts | — | 132 | — | 119 |
| (Sagamoto) human fibroblasts | — | 116 | — | 188 |
| (SA$_6$) normal rat kidney | — | 103 | — | 94 |
| Nonhuman | | | | |
| CCl 64 mink lung | 96 | — | 93 | — |
| SR Balb/C (Schmidt Rupin-RSV transformed) | 15 | — | — | — |

As indicated in Table 1 relative to the various human tumor cell lines tested, the human lung carcinoma lines, A549 and 2981, exhibited the most sensitivity to inhibition, 55% and 48% and 52% and 46%, respectively, for CIF-A and CIF-B. Likewise, a melanoma and breast carcinoma were also effective target cells. To a lesser extent, various degrees of inhibition were also observed with an epidermoid carcinoma line (A431), 28% and 24%, respectively, for CIF-A and CIF-B. Some lines exhibited minimum or no sensitivity to either CIF-A or CIF-B; i.e., in the rhabdomyosarcoma line A673 (late passage), no detectable inhibition was seen at any concentration tested. The inhibition activity of CIFs is not limited to cells of human origin, but also was (as shown in FIG. 1) pronouced in the mink epithelial line CCl 64 (>90%) but minimally observed in murine cells transformed by the Schmidt Rupin strain of Rous sarcoma virus (SR Balb/C). In contrast, some untransformed cell lines were stimulated rather than inhibited by either CIF-A or CIF-B. Both human lung (WI 38) and Sagamoto fibroblasts exhibited a stimulation in DNA synthesis: 132% and 119% for WI 38, 116% and 188% for Sagamoto fibroblasts, respectively, for CIF-A and CIF-B. Normal rat kidney cultures were also stimulated at concentrations which inhibited tumor cell targets.

EXAMPLE 3

The activity of CIF-A and CIF-B as oncostats was tested on human lung carcinoma cells (A549) using the Soft Agar Assay described above. The cells ($2 \times 10^4$) were mixed with homogeneous preparations of either CIF-A or CIF-B at various concentrations. The results are reported in Table 2 below. Values of soft agar colonies represent the average number of colonies >20 cells in diameter per eight random low power fields scored 10 days after seeding.

TABLE 2

Effect of CIF-A and CIF-B on the growth of human lung carcinoma cells in soft agar

| | Soft agar colonies | |
|---|---|---|
| | CIF-A | CIF-B |
| Control (no additions) | 328 | 275 |
| CIFs (ng/ml) | | |
| 0.50 | 292 | 237 |
| 1.0 | 260 | 224 |
| 5.0 | 188 | 114 |
| 10.0 | 110 | 108 |
| 20.0 | 73 | 54 |

As shown in Table 2, plates seeded with tumor cells containing as little as 1.0 ng/ml of CIF-A or CIF-B start to show a reduction in number of colonies. The reduction of colony size is even more striking at these low concentrations. Half-maximal inhibition in number of colonies is seen at approximately 5 ng/ml with either CIF-A or CIF-B (a 52% and 47% reduction for CIF-A and CIF-B, respectively). At a concentration of 20 ng/ml, residual colonies observed were no more than 20-30 cells in size.

EXAMPLE 4

Additional tests were carried out using the soft agar assay to evaluate the oncostatic activity of CIF-A and CIF-B on an anchorage-independent growth of primary human tumor cells in agar (Table 3). The CIFs were tested at 10 and 100 ng/ml. Four different adenocarcinomas derived from breast and ovarian tissue, one lymphoma, and one tumor of unknown etiology were tested. CIF-B proved to be the more potent oncostat in these tests, exhibiting 100% inhibition of colony formation on 3 of 4 adenocarcinomas tested and 90% inhibition on the other. The inhibition provided by CIF-A at equivalent concentrations ranged from 60-97%. CIF-B inhibited these cells 70% and 95% when tested at equivalent concentrations. The tumor cells of unknown etiology were also more effectively inhibited by CIF-B than by CIF-A.

Interestingly, several of the tumor cells tested were defractory to inhibition of proliferation by 18 different chemotherapeutic drugs, including adriamycin, platinum, and 5-fluorouracil, and yet these same cells were exquisitely sensitive to CIF-B, showing 100% inhibition at a factor concentration of 100 ng/ml. Under conditions in which the inhibition of cell proliferation was comparable for CIF-A and CIF-B, and for certain chemotherapeutic drugs such as 5-fluorouracil and platinum, the biologically active peptides were 10,000 to 100,000 more potent than the drugs on a molar basis.

TABLE 3

| Specimen Number | Site | Type | CIF A 10 | CIF A 100 | CIF B 10 | CIF B 100 | (ng/ml) |
|---|---|---|---|---|---|---|---|
| 86-0393 | Breast | Adeno | 79 | 18 | 30 | 0 | |
| 86-0394 | | Lymphoma | 31 | 15 | 5 | 0 | |
| 86-0395 | Ovary | Adeno | 19 | 3 | 3 | 0 | |
| 86-0396 | Ovary | Adeno | 68 | 39 | 52 | 10 | |
| 86-0397 | Ovary | Adeno | 52 | 24 | 14 | 0 | |
| 86-0399 | Unk | | 51 | 26 | 31 | 8 | |

Modifications of the above described modes of carrying out the invention that are obvious to those of skill in the fields of protein chemistry, oncology, pharmacology, and related fields are intended to be within the scope of the following claims.

We claim:

1. A method of inhibiting growth of tumor cells in a mammal comprising administering an oncostatically effective amount of CIF-B to a mammal having tumor cells sensitive to CIF-B.

2. The method of claim 1 wherein the tumor cells are carcinoma cells, adenocarcinoma cells, melanoma cells, or lymphoma cells.

3. The method of claim 1 wherein the carcinoma cells are breast, lung, colon or ovarian carcinomas.

* * * * *